United States Patent [19]

Remiszewski et al.

[11] Patent Number: 5,199,419
[45] Date of Patent: Apr. 6, 1993

[54] SURGICAL RETRACTOR

[75] Inventors: Stanley H. Remiszewski, Greenwich; Paul A. Matula, Brookfield; H. Jonathan Tovey, Milford, all of Conn.

[73] Assignee: United States Surgical Corporation, Norwalk, Conn.

[21] Appl. No.: 740,443

[22] Filed: Aug. 5, 1991

[51] Int. Cl.$^5$ .............................................. A61B 17/02
[52] U.S. Cl. .................................. 128/20; 606/198
[58] Field of Search .................... 128/20, 17, 4, 7; 606/198, 191, 205, 206

[56] References Cited

U.S. PATENT DOCUMENTS

| | | |
|---|---|---|
| 972,983 | 10/1910 | Arthur . |
| 1,244,741 | 10/1917 | McCleary . |
| 1,328,624 | 1/1920 | Graham . |
| 2,202,748 | 5/1940 | Solo ........................ 128/20 |
| 2,816,552 | 12/1957 | Hoffman . |
| 3,313,294 | 4/1967 | Uddenberg . |
| 3,467,079 | 9/1969 | James . |
| 4,190,042 | 2/1980 | Sinnreich . |
| 4,226,228 | 10/1980 | Shin et al. . |
| 4,459,978 | 7/1984 | Kotsanis . |
| 4,559,944 | 12/1985 | Jaeger ................ 606/205 X |
| 4,580,568 | 4/1986 | Gianturco ............ 606/198 |
| 4,654,028 | 3/1987 | Suma . |
| 4,655,219 | 4/1987 | Petruzzi ................ 128/6 X |
| 4,656,999 | 4/1987 | Storz .................... 128/4 |
| 4,765,311 | 8/1988 | Kulik et al. . |
| 4,945,920 | 8/1990 | Clossick .............. 606/205 X |
| 4,990,156 | 2/1991 | Lefebvre .............. 606/191 X |
| 4,994,079 | 2/1991 | Genese et al. ......... 128/6 X |
| 5,052,402 | 10/1991 | Bencini et al. ......... 606/206 X |
| 5,098,440 | 3/1992 | Hillstead .............. 128/4 X |
| 5,113,846 | 5/1992 | Hiltebrandt et al. . |

FOREIGN PATENT DOCUMENTS 736949  5/1980  U.S.S.R. ................ 606/198
1360708 12/1987 U.S.S.R. ................ 128/20

OTHER PUBLICATIONS

Sklar, "Surgical Instruments", Apr. 1975, p. 100.
"Levy Articulating Retractor", Surgical Products, p. 33, Jun. 1992 edition.

Primary Examiner—Richard J. Apley
Assistant Examiner—Karen A. Jalbert
Attorney, Agent, or Firm—Thomas R. Bremer; Peter G. Dilworth; Rocco S. Barrese

[57] ABSTRACT

A novel surgical retractor is provided including a handle assembly, a housing and a collapsible retractor assembly connected to a distal end of the housing. The handle assembly includes a stationary handle in cooperation with an actuating structure for manipulating the collapsible retractor assembly through the housing.

The handle assembly may be configured in a variety of forms including palm grips, pistol grips, axial grips, ring grips, etc. The housing includes a tubular structure having an inner tube axially disposed within an outer tube. The outer tube is fixed in the stationary handle with the inner tube passing through the outer tube and connected to the actuating structure. Where desired, either the outer or inner tube may be rotatably attached to the stationary handle. The retractor assembly is attached to the distal end of the housing and includes a reciprocal yoke assembly interconnected with a plurality of collapsible interleaved retractor blades. One element of the yoke assembly is typically maintained stationary while the other is allowed to reciprocate axially to deploy the interleaved retractor blades into a fan configuration.

58 Claims, 12 Drawing Sheets

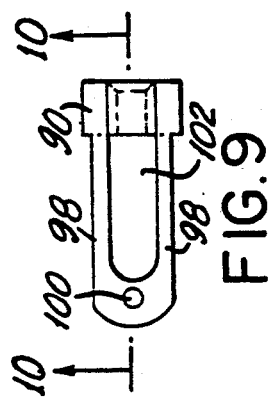
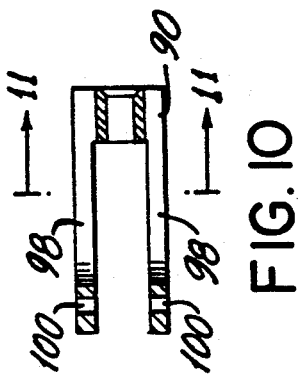
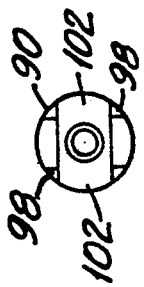
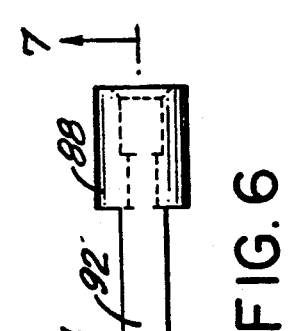
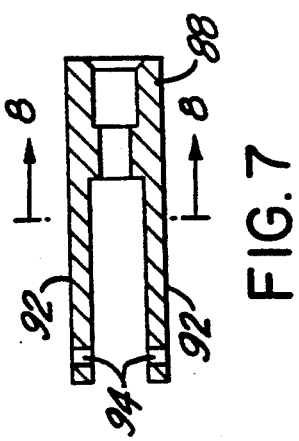
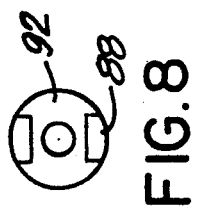

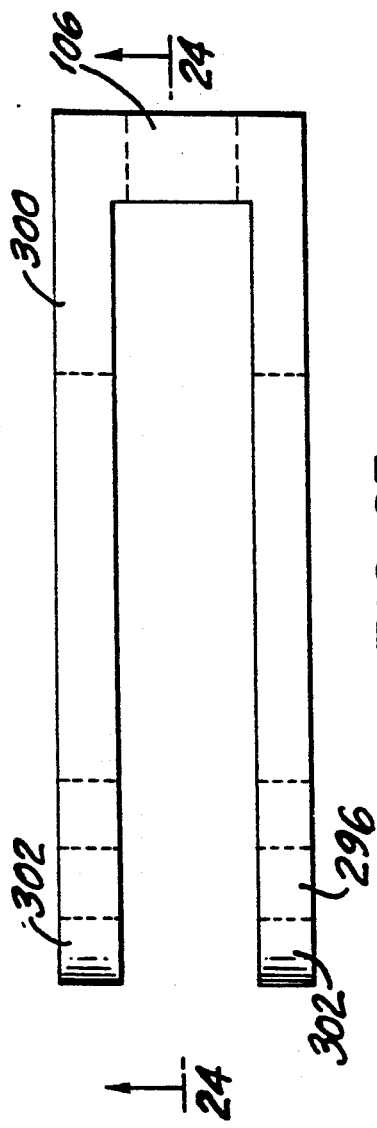
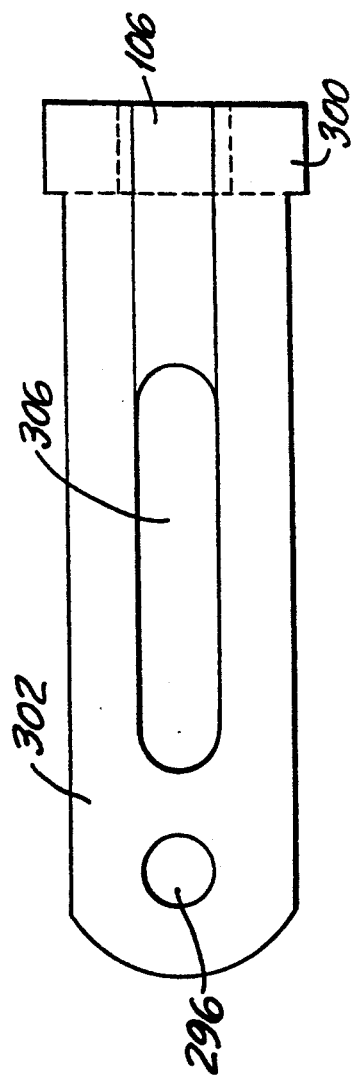
FIG. 23
FIG. 24

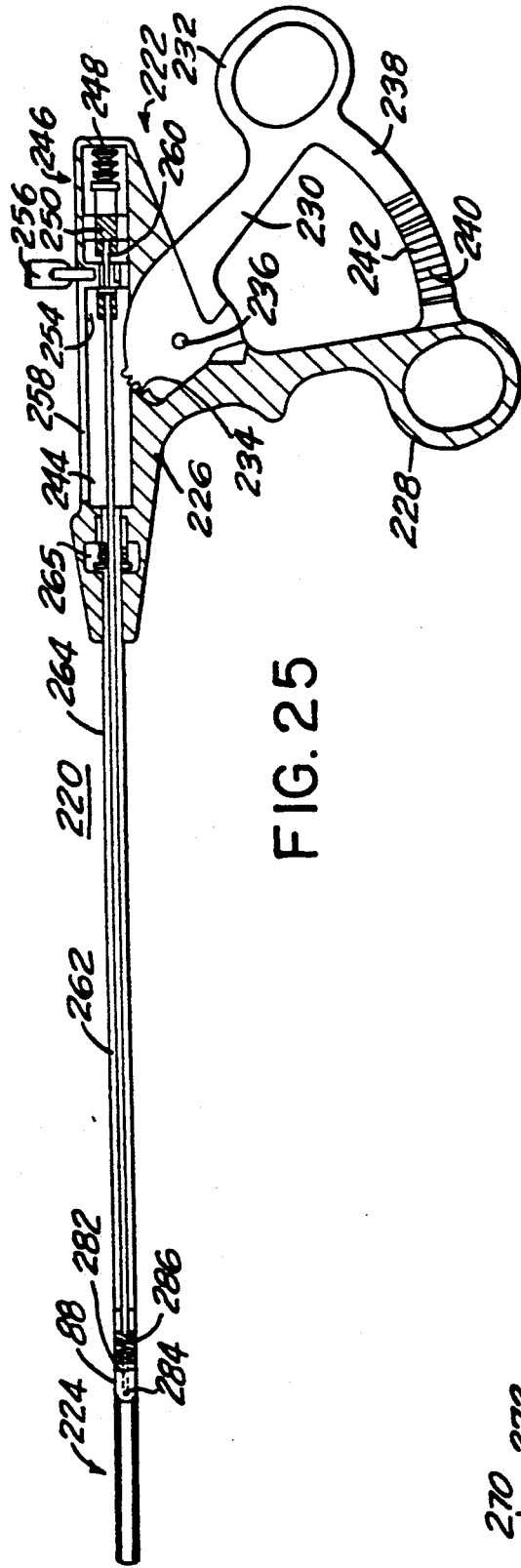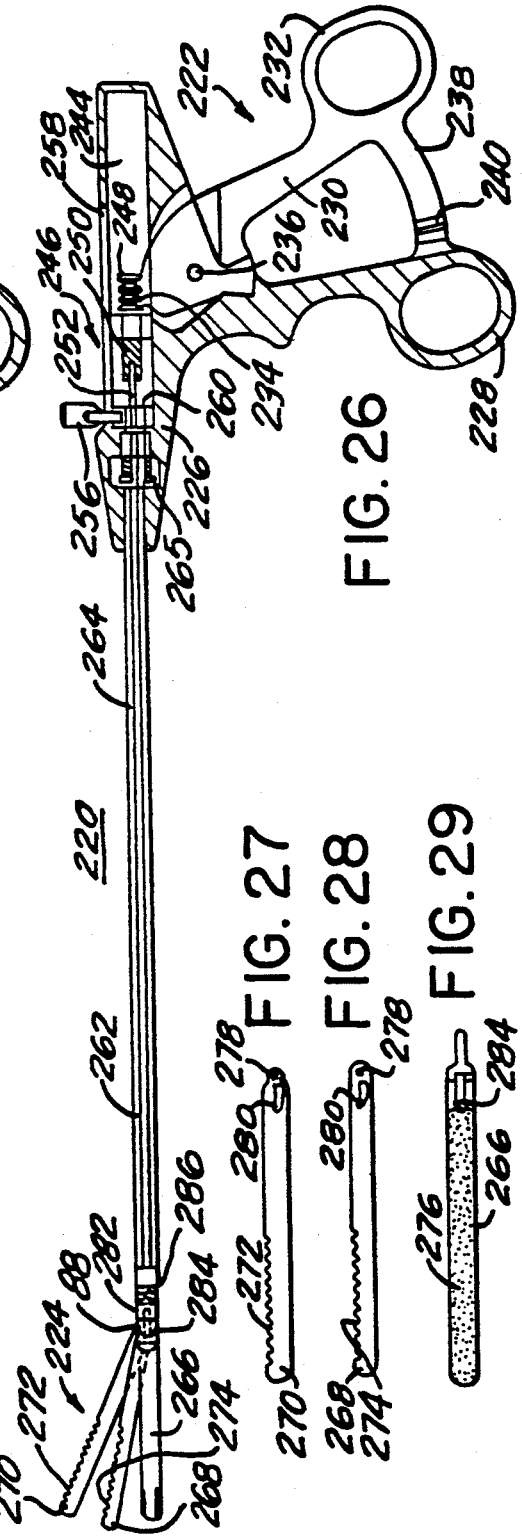

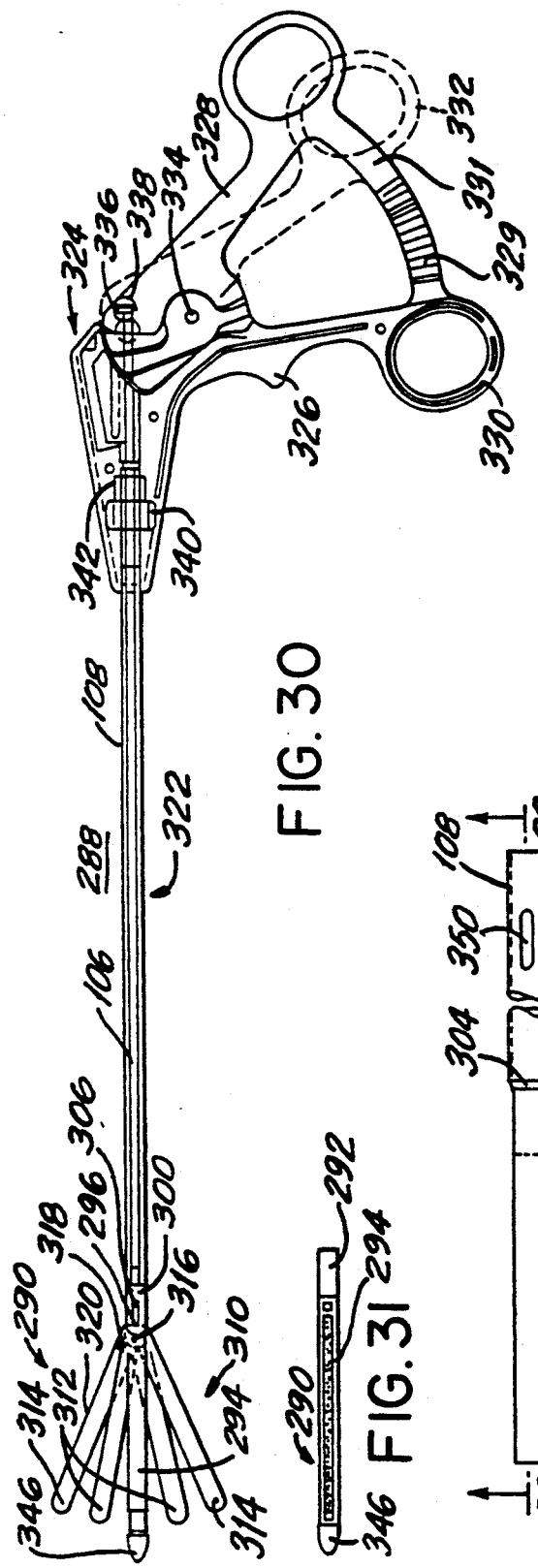

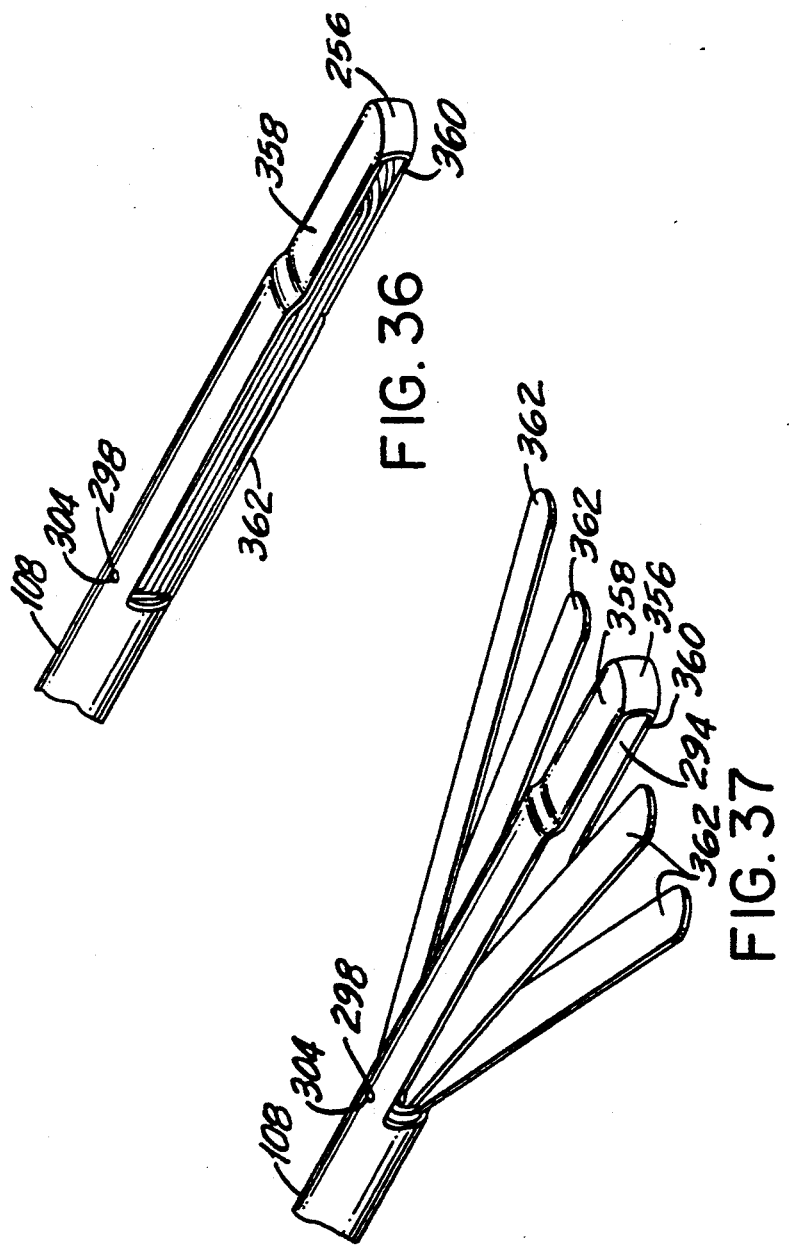

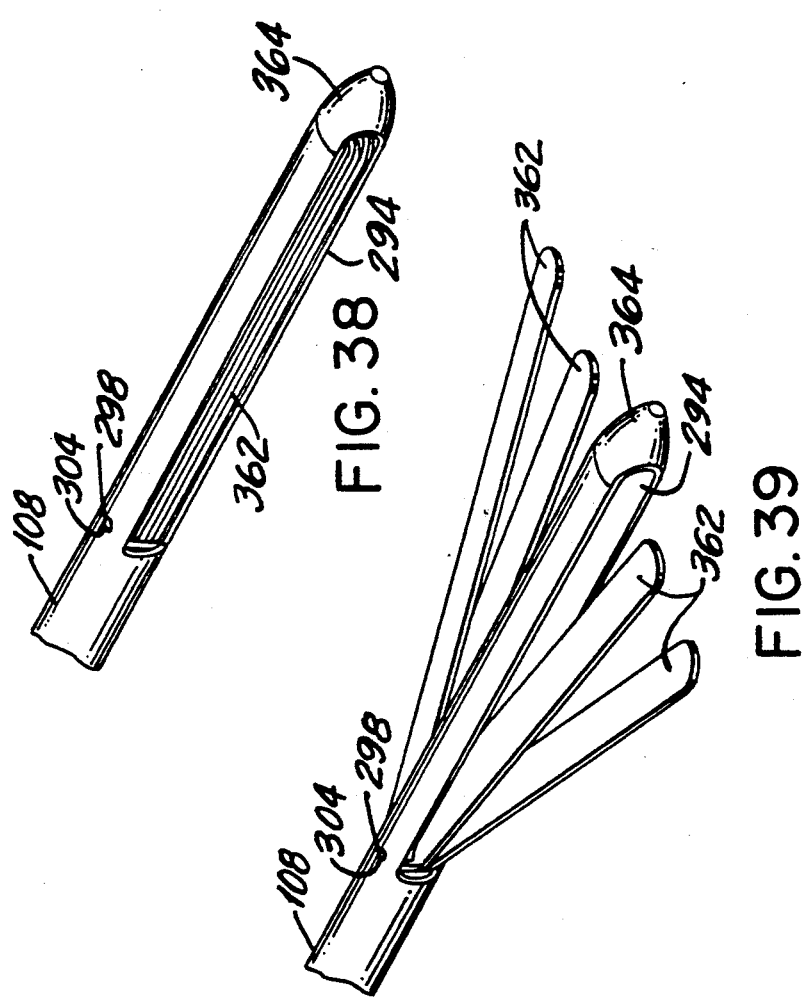

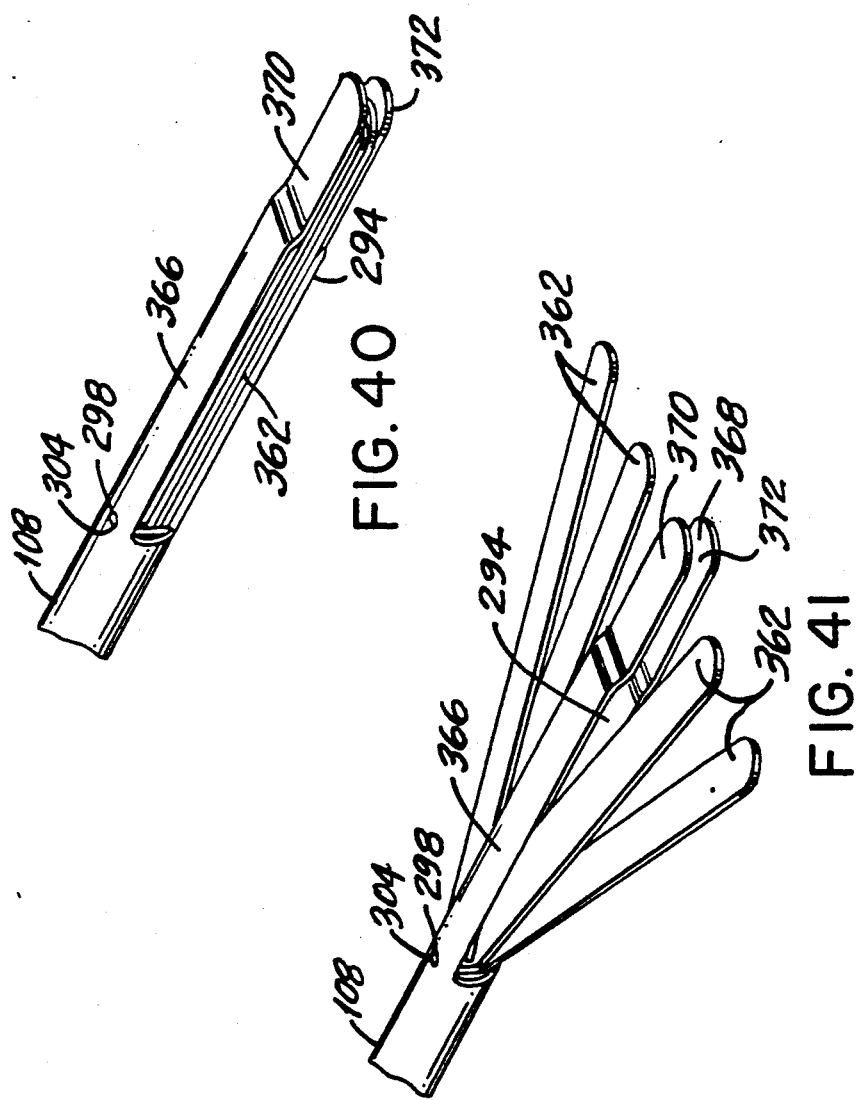

SURGICAL RETRACTOR

BACKGROUND OF THE INVENTION

1. Field of the Invention

This invention relates generally to surgical instrumentation and, more particularly, to a surgical retractor having deployable blades for use with endoscopic or laparoscopic devices in performing examinations or surgical procedures within body cavities.

2. Description of Related Art

Endoscopic or laparoscopic procedures are characterized by the provision of an elongated cannula structure having a relatively thin diameter with a proximal and distal end. The distal end is passed through the surrounding tissue into the body cavity wherein the surgical procedure or examination is to be effected, thus providing a conduit for the insertion of surgical instrumentation. A plurality of cannula structures may be used to allow operation of a variety of instruments simultaneously during a given procedure.

In conventional surgical procedures the function of holding tissue and organs in a given location to facilitate access and viewing is typically accomplished by a retractor. This instrumentation is ordinarily in the form of a broad paddle structure or multiple fingers attached to a handle. See, for example, U.S. Pat. No. 3,467,079 (James). This structure, however, is not usable in endoscopic procedures because the retractor is too large to be insertable through the cannula structure into the operative body cavity.

Collapsible intralumen expanders or retractors have taken the form of radial fingers which are activatable to extend relative to each other upon entering the body cavity. See, for example, U.S. Pat. Nos. 4,654,028 (Suma), 4,459,978 (Kotsanis). Dilators of this type are also known. See, for example, U.S. Pat. Nos. 1,328,624 (Graham) and 972,983 (Arthur). In each case, once the retractive or dilatory function is completed, the fingers are compressed and withdrawn. Another collapsible retractor structure includes a pair of collapsible fingers joined by a web of resilient material which, upon insertion into the cannula structure, can expand to form a retractive structure. See, for example, U.S. Pat. No. 4,190,042 (Sinnreich).

Greatly improved retractor structure has been developed and is described in commonly assigned co-pending patent application Ser. No. 07/634,482 filed Dec. 27, 1990. That structure shows a plurality of interleaved retractor blades mounted in a tubular housing. The blades are movable between a closed position and an open position to facilitate ease of insertion and deployment through a cannula.

SUMMARY OF THE INVENTION

It is an object of the present invention to provide a surgical retractor which overcomes the drawbacks and deficiencies associated with prior art retractors.

Another object of the present invention is to provide a surgical retractor adapted for use in endoscopic and laparoscopic procedures.

A further object of the present invention is to provide a surgical retractor which is easily deployable within a body cavity to provide a retractive function therein.

The present invention provides a novel surgical retractor which has advantageous specific applications in endoscopic and laparoscopic surgical procedures and examinations. The surgical retractor includes a handle assembly, a housing means and a collapsible retractor assembly connected to a distal end of the housing means.

The handle assembly includes a handle in cooperation with an actuating structure for manipulating the collapsible retractor assembly through the housing means in response to relative motion between the actuating structure and the handle. The handle assembly may be configured in a variety of forms including palm grips, pistol grips, axial grips, ring grips, etc.

The housing means, in its most basic embodiment, comprises an elongated tubular structure having an inner tube axially disposed within an outer tube. The outer tube is typically fixed in the stationary handle with the inner tube passing through the outer tube and connected to the actuating structure. The inverse of this configuration, i.e., the inner tube fixed to the stationary handle with the outer tube connected to the actuating structure, is equally useful. Where independent rotation of the tubular housing is desired, the outer tube or inner tube may be rotatably attached to the stationary handle.

A retractor assembly is attached to the distal end of the housing means and includes a reciprocal yoke assembly interconnected with a plurality of collapsible interleaved retractor blades. One element of the yoke assembly is usually maintained stationary while the other is allowed to reciprocate axially to deploy the interleaved retractor blades into a fan configuration.

In alternate embodiments an enclosure tube is provided surrounding the inner and outer tubes. In order to deploy the interleaved retractor blades, the blades are first moved out of the distal end of the enclosure tube.

BRIEF DESCRIPTION OF THE DRAWINGS

The foregoing objects and other features of the invention will become more readily apparent and may be understood by referring to the following detailed description of preferred embodiments, taken in conjunction with the accompanying drawings forming a part hereof.

FIG. 6 is a top view of the pivot yoke assembly for a preferred embodiment of the present invention.

FIG. 7 is a side view of the pivot yoke assembly taken through line 7—7 of FIG. 6.

FIG. 8 is an end view of the pivot yoke assembly taken through line 8—8 of FIG. 7.

FIG. 9 is a top view of the slide yoke assembly for a preferred embodiment of the present invention.

FIG. 10 is a side view of the slide yoke assembly taken through line 10—10 of FIG. 9.

FIG. 11 is an end view of the slide yoke assembly taken through line 11—11 of FIG. 10.

FIG. 23 is a side view of a pivot yoke in accordance with a preferred embodiment of the present invention.

FIG. 24 is a top view of a pivot yoke taken along line 24—24 of FIG. 23.

FIG. 25 is a side view in partial cross section of a preferred embodiment of a closed surgical retractor in accordance with the present invention.

FIG. 26 is a side view in partial cross section of the surgical retractor of FIG. 25 with the retractor blades in the deployed position.

FIGS. 27-29 show preferred embodiments of retractor blades for use with the present invention.

FIG. 30 is a side view in partial cross section of a preferred embodiment of an open surgical retractor in accordance with the present invention.

FIG. 31 is a side view of the retractor assembly of the surgical retractor of FIG. 30 in the closed position.

FIG. 32 is a top view of the retractor assembly having a blunt end.

FIG. 33 is a side view of the retractor assembly of FIG. 32 through line 33—33.

FIG. 34 is a side view of the retractor assembly having a hollow end.

FIG. 35 is a top view of the retractor assembly of FIG. 34 taken through line 35—35.

FIG. 36 is a perspective view of a preferred embodiment of the retractor assembly in the closed position.

FIG. 37 is a perspective view of the retractor assembly of FIG. 36 in the deployed position.

FIG. 38 is a perspective view of a preferred embodiment of the retractor assembly in the closed position.

FIG. 39 is a perspective view of the retractor assembly of FIG. 38 in the deployed position.

FIG. 40 is a perspective view of a preferred embodiment of the retractor assembly in the closed position.

FIG. 41 is a perspective view of the retractor assembly of FIG. 40 in the deployed position.

DETAILED DESCRIPTION OF PREFERRED EMBODIMENTS

Figure 1:
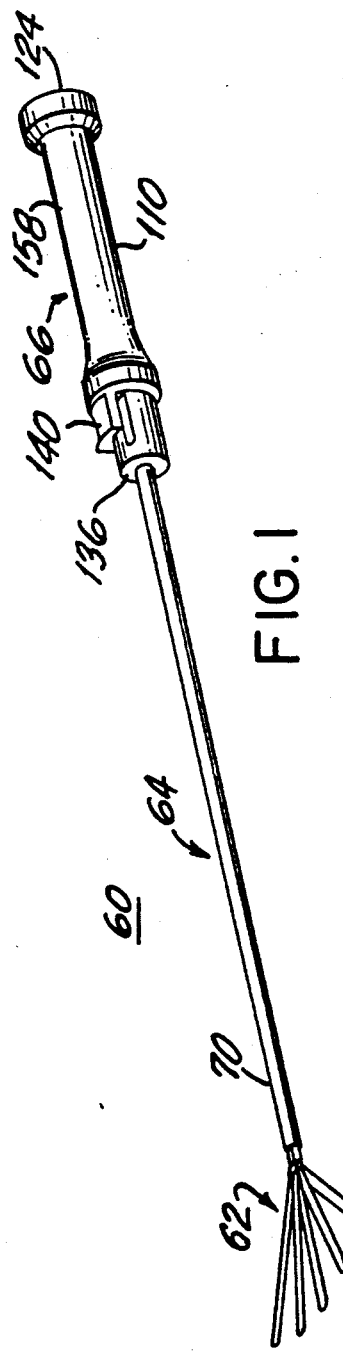
FIG. 1 is a perspective view of a preferred embodiment of the present invention.
Figure 2:
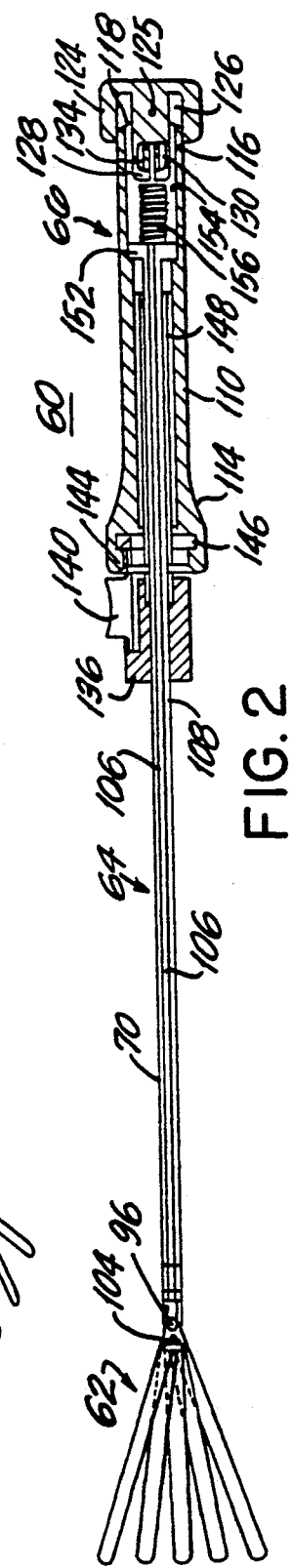
FIG. 2 is a side view in cross section of a preferred embodiment of the present invention with the retractor blades deployed in a fan configuration.
Figure 3:
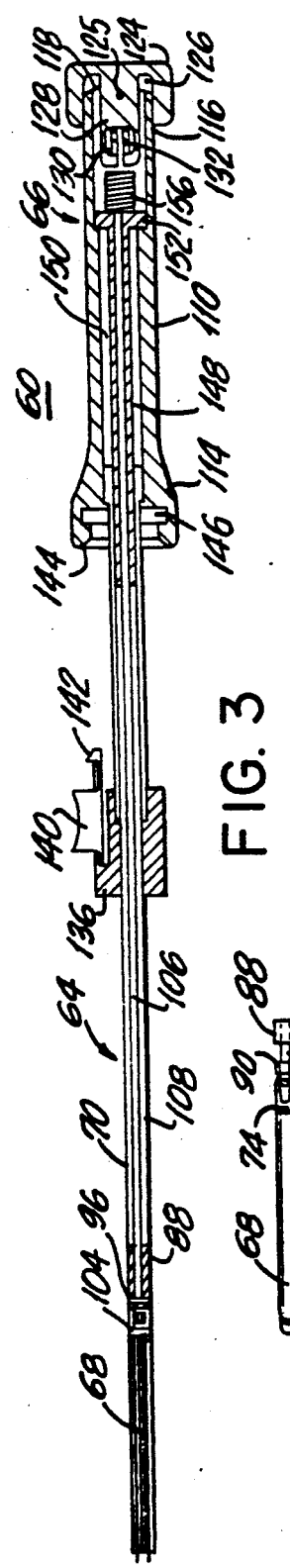
FIG. 3 is a side view in cross section of a preferred embodiment of the present invention with the retractor blades folded and enclosed by an enclosure tube.

Referring now in specific detail to the drawings, in which like reference numbers identify similar or identical elements, FIGS. 1-3 illustrate a preferred embodiment of a surgical retractor, shown generally at 60. The retractor 60 can be broken down into a retractor assembly 62, elongated tubular housing means 64 and handle means 66. The embodiment of FIGS. 1-3 is adapted for and particularly useful in endoscopic or laparoscopic procedures wherein at least an endoscopic portion of the surgical retractor 60 is inserted into the operative site through a cannula (not shown).

Figure 4:
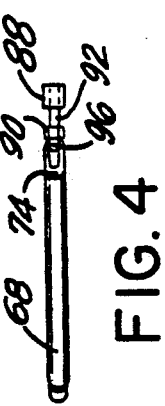
FIG. 4 is a side view of the retractor blades and the reciprocal yoke assembly for the surgical retractor of FIGS. 1-3.
Figure 5:
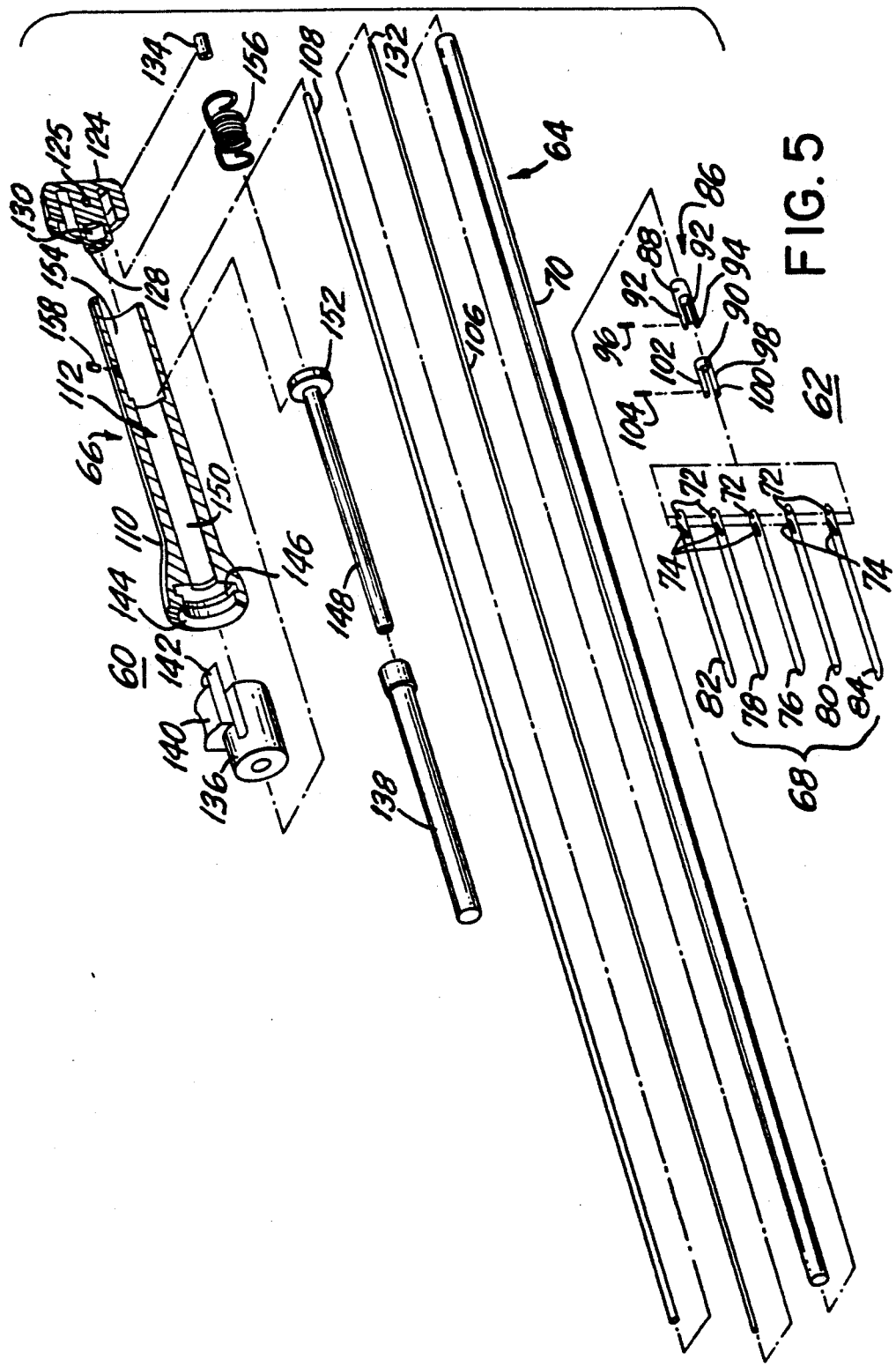
FIG. 5 is an exploded perspective view of a preferred embodiment of the present invention.
Figure 12:
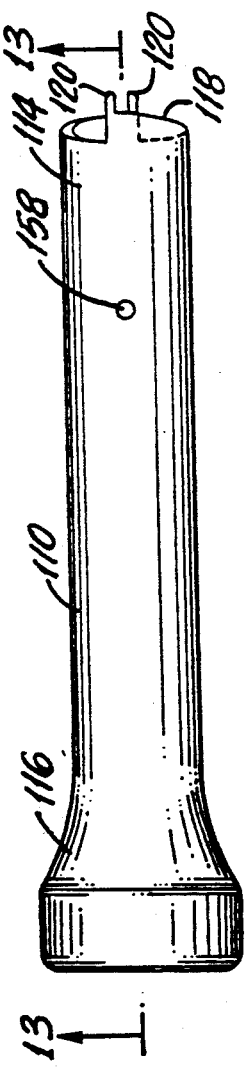
FIG. 12 is a top view of a handle in accordance with a preferred embodiment of the present invention.
Figure 13:
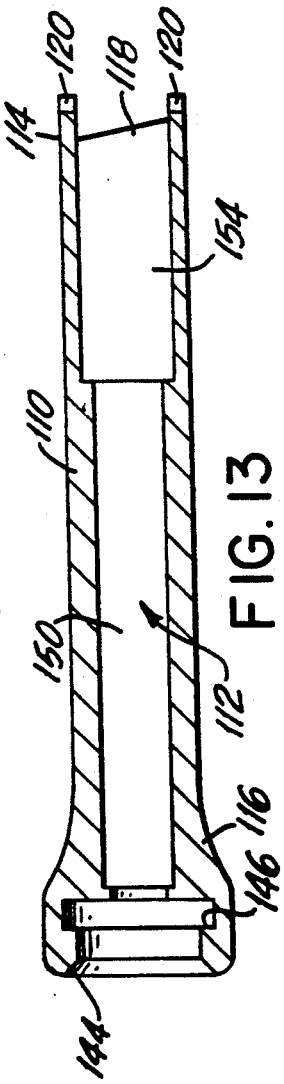
FIG. 13 is a side view of a handle taken along line 13—13 of FIG. 12.
Figure 15:
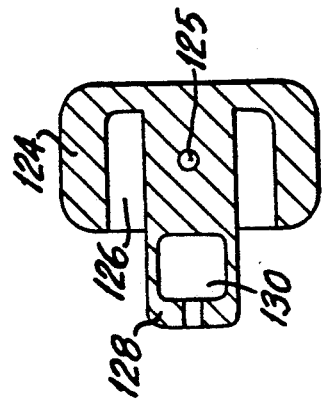
FIG. 15 is a side view in cross section of the rotation knob.
Figure 14:
FIG. 14 is an unfolded end view of a proximal end of the handle of FIG. 12 incorporating progressive stops in the camming surfaces.

The retractor assembly 62 generally comprises a plurality of interleaved elongated blades 68 disposed in stacked relation and pivotally deployable about a proximal end to form an interleaved fan configuration (FIG. 2). This fan configuration can be readily adapted to different shapes and uses by either varying the number or size of the blades 68 or their respective angles of deployment. In the closed stacked position, the blades 68 fold in upon each other in axial alignment (FIGS. 3 and 4). In the embodiment of FIGS. 1-3, the retractor assembly 62 is contained within an enclosure tube 70 prior to deployment (FIG. 3) as will be discussed in greater detail below.

Referring to FIGS. 5-11, each of the blades (collectively referred to as 68) of the retractor assembly is provided with a fixed pivot hole 72 in a proximal end thereof. A camming slot 74 is located distal to the pivot hole 72 and is formed at predetermined angles to effect proper deployment of the retractor assembly 62. In the embodiment of FIGS. 1-5, for example, center blade 76 is provided with an axially aligned camming slot to maintain the blade in a fixed axial orientation. The blades positioned adjacent center blade 76, i.e. blades 78, 80, cam outward in opposing directions to a predetermined angle with respect to the longitudinal plane of the center blade 76. Similarly, the outermost blades, i.e. 82, 84, have camming slots which cause the blades to move in opposing directions to a predetermined angle greater than that of blades 78 and 80 so as to form a fan configuration which deploys outward respectively from the center blade 76.

Blades 68 are interconnected by a unique reciprocal yoke assembly 86 (FIGS. 5-11) including a pivot yoke 88 (FIGS. 6-8) and a slide yoke 90 (FIGS. 9-11). Referring to FIGS. 5-8, pivot yoke 88 includes a pair of parallel axially extending arms 92 containing a transverse bore 94 in a distal end thereof. Pin 96 extends through transverse bore 94 and each of the fixed pivot holes 72 formed in the proximal ends of blades 68. Thus blades 68 are free to pivot about pin 96 in pivot yoke 88.

Slide yoke 90 includes a pair of axially extending parallel arms 98, each having a transverse bore 100 formed in a distal end thereof. Each parallel arm 98 is further provided with a longitudinal channel 102 adapted and configured to receive parallel arms 92 of the pivot yoke 88 therein. Pin 104 extends through transverse bore 100 and camming slots 74 in blades 68. As the pivot yoke 88 and slide yoke 90 move reciprocally relative to one another in channel 102, the movement of pin 104 in camming slots 74 effects the deployment and closure of blades 68.

Referring to FIGS. 1-3 and 5, elongated tubular housing means 64 includes a center rod 106 disposed within a guide tube 108. In the present embodiment, an enclosure tube 70 serves to at least partially enclose the combined center rod 106 and guide tube 108. Slide yoke 90 is provided with an axial bore 110 for fixedly receiving a distal end of center rod 106. Pivot yoke 88 has an axial bore 112 aligned with bore 110 to permit center rod 106 to reciprocally move slide yoke 90 with respect to pivot yoke 88. Pivot yoke 88 is fixed to the distal end of guide tube 108 (FIG. 5) and serves to pivotally hold blades 68 in place.

Referring now to FIGS. 5 and 12-15, handle means 66 comprises an axially aligned, substantially cylindrical housing 110 having a central bore 112 extending from a proximal end 114 to a distal end 116. At the proximal end, a helical camming surface 118 is provided with integral stopping tabs 120. See FIGS. 12-14. Where desired, intermediate grooves 122 may be formed in the helical camming surface 118 to provide sequential stops in the deployment of the retractor assembly 62. See FIG. 14.

Deployment knob 124 (FIG. 15) interfits into the proximal end 114, of cylindrical housing 110 with the helical camming surface 118 at least partially contained in annular channel 126. A center projection 128 contains a cavity 130 for receiving and securing a proximal end 132 of center rod 106. Capping element 134 attaches to end 132 and is adapted to be securely retained within cavity 130 while allowing deployment knob 124 to rotate. A transverse camming pin 125 is mounted in deployment knob 124 with a portion of the pin 125 extending into annular channel 126 to engage helical camming surface 118.

A clasp knob 136 is fixed to outer bushing 138 and serves to retract and extend enclosure tube 70. Both clasp knob 136 and outer bushing 138 are fixed to enclosure tube 70 and move axially reciprocally therewith to cover and uncover the retractor assembly 62. Clasp knob 136 is provided with a transversely flexible locking member 140 having a hooked locking tab 142 attached thereto. This locking tab 142 is adapted to be transversely cammed by flange 144 in housing 110 and to abut and engage an inner surface 146 of flange 144. See FIGS. 2, 3 and 5.

Outer bushing 138 telescopically engages inner bushing 148 and is axially movable along the inner bushing 148. A cylindrical cavity 150 is formed in housing 110 to accommodate both the inner bushing 148 and the outer bushing 138. Inner bushing 148 is provided with a flange 152 at a proximal end, which flange 152 travels axially in cavity 154 in a proximal end of housing 110. An extension spring 156 is disposed in cavity 154 between flange 152 and center projection 128 of deployment knob 124. This extension spring 156 serves to apply an axial distal force on the flange 152 of inner bushing 148 which force is transmitted through the flange to center projection 128 of deployment knob 124. This axial distal force maintains pressure on camming pin 125 against helical cam 118. A set screw 158 is provided in housing 110 to limit travel of flange 152 in cavity 154.

To deploy the retractor assembly 62 of this embodiment of the present invention from the closed position (FIG. 3), clasp knob 136 is moved proximally until hooked locking tab 142 just abuts flange 144. At this point, the proximal end of outer bushing 138 abuts flange 152 of inner bushing 148 and the hooked locking tab 142 of transversely flexible locking member 140 engages inner surface 146 of flange 144 thus locking enclosure tube 70 in the retracted position. See FIG. 2.

Thereafter, deployment knob 124 is rotated, driving transverse camming pin 125 along helical camming surface 118 formed in the proximal end 114 of cylindrical housing 110. This action moves deployment knob 124 proximally with respect to cylindrical housing 110 and drawing center rod 106 in a proximal direction with respect to guide tube 108. As center rod 106 moves proximally, pivot yoke 86 retracts in channels 102 of slide yoke 90 causing pin 96 to cam in camming slots 74 of retractor blades 68 which, simultaneously pivot in a predetermined configuration about pin 104 in slide yoke 90.

Closure of the retractor assembly 62 is accomplished simply by rotating deployment knob 124 in the opposite direction to bring blades 68 into a stacked interleaved position. Transversely flexible locking member 140 is depressed to disengage hooked locking tab 142 from the inner surface 146 of flange 144. Thereafter, transversely flexible locking tab 142 is moved distally until enclosure tube 70 covers at least a portion of the closed retractor assembly 62. See FIG. 3.

Figure 16:
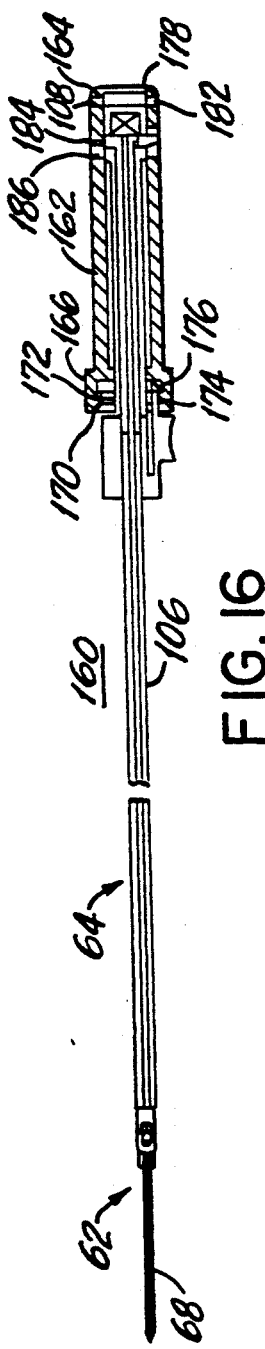
FIG. 16 is a side view in cross section of a surgical retractor in accordance with a preferred embodiment of the present invention.
Figure 17:
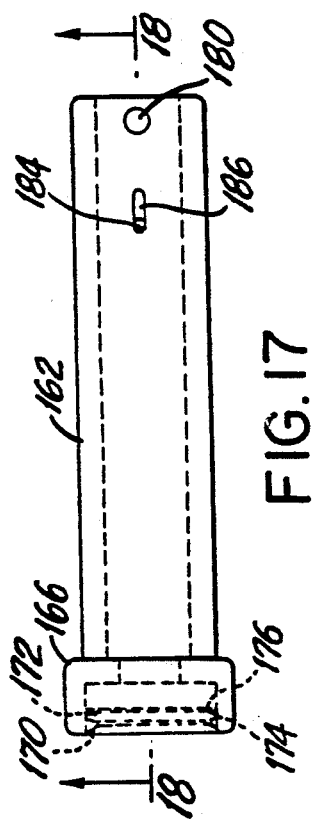
FIG. 17 is a top view of a handle in accordance with the surgical retractor of FIG. 16.
Figure 18:
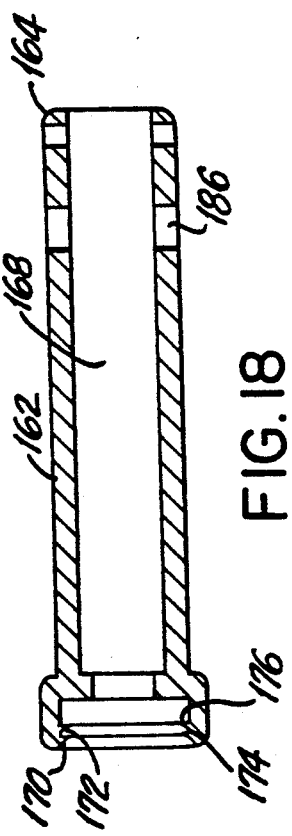
FIG. 18 is a side view of a handle taken along line 18—18 of FIG. 17.
Figure 19:
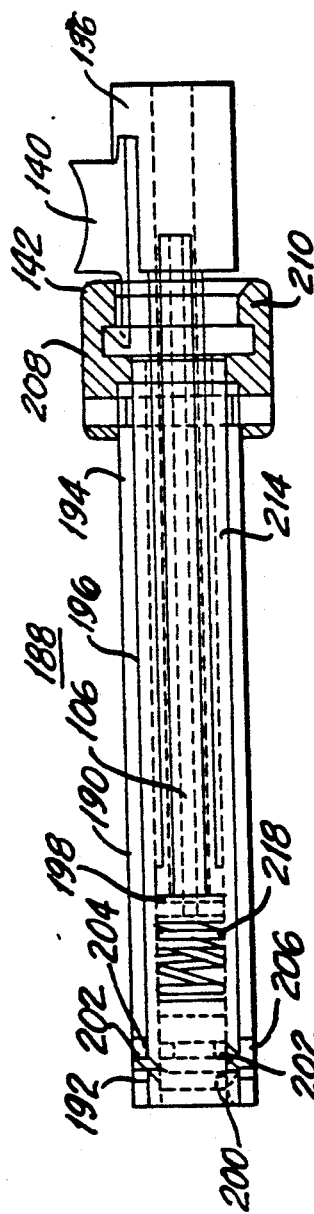
FIG. 19 is a side view in cross section of a handle assembly in accordance with a preferred embodiment of the present invention.
Figure 21:
FIG. 21 is an end view of the barrel cam of FIG. 20 taken along line 21—21.
Figure 20:
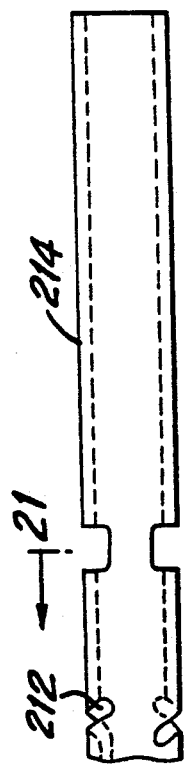
FIG. 20 is a side view of a barrel cam structure for use in the handle assembly of FIG. 19.
Figure 22:
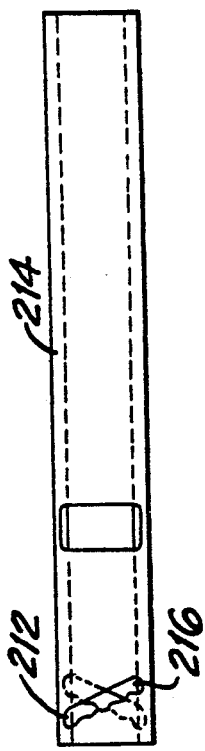
FIG. 22 is a side view of a barrel cam structure having progressive stops formed into the camming surfaces.

Referring to FIGS. 16-18, a variation of the embodiment of the surgical retractor of FIGS. 1-16 is shown. The surgical retractor, shown generally at 160, includes the same basic subgroups discussed above including a retractor assembly 62, an elongated tubular housing means 64 and a handle means 66.

The retractor assembly 62 and the elongated tubular housing means 64 are substantially similar in construction and operation as those of the surgical retractor 60 discussed above. Handle means 66, however, differs in some structural aspects. A cylindrical housing 162 having a proximal end 164 and a distal end 166 with a central bore 168 therethrough is provided. The bore 168 is restricted in size near distal end 166 of housing 162 and is substantially open at the proximal end 164. See FIG. 18. A pair of annular flanges 170, 172 are axially sequentially disposed in the distal end 166 of housing 162, each such flange defining a respective inner surface 174, 176. Inner and outer bushings, 148 and 138 respectively, are configured and operate substantially the same as those described above with respect to FIGS. 1-15. Center rod 106, however, is fixed to disk 178 which is anchored in the opening 180 in the proximal end 164 of housing 162 by means of set screws 180, 182. A compression spring 156 is disposed between flange 152 of inner bushing 148 and disk 178 and, when compressed, imparts a distal axial force to move clasp knob 136 and the attached enclosure tube 70 distally. Flange 152 is limited in axial movement by pin 184 extending transversely from the outer edge of flange 152 into axial slot 186.

To deploy the retractor assembly 62 of this surgical retractor 160 from the closed position, clasp knob 136 is moved in a proximal direction exposing retractor assembly 62. Hooked locking tab 142 of transversely flexible locking member 140 engages the inner surface 174 of distalmost annular flange 170 effectively locking enclosure tube 70 in its most proximal position. Continued proximal motion of clasp knob 136 causes outer bushing 138 to engage inner bushing 148 and move inner bushing proximally with respect to center rod 106. This motion causes the retractor assembly 62 to deploy in a manner substantially the same as that set forth above with respect to the embodiment of FIGS. 1-15. At its proximalmost position, the hooked locking tab 142 of transversely flexible locking member 140 engages the inner surface 176 of proximalmost annular flange 172 thus locking the blades 68 in a deployed fan configuration.

Referring now to FIGS. 19-22, further variation of the handle means of the preferred embodiment of FIGS. 1-15 is shown. The handle means 188 includes a cylindrical housing 190 having a proximal end 192 and a distal end 194 with a central bore 196 therethrough. A clasp knob 136 attached to an outer bushing 138 and an enclosure tube 70 serves to effect proximal and distal motion of the enclosure tube in substantially the same way as that described above. An inner bushing 148 connects to guide tube 108 and has an axial bore 198 disposed therein to allow passage of center rod 106. Movable block 200 engages and holds a proximal end of center rod 106 for limited axial reciprocal motion. A transverse camming pin 202 extends through movable block 200 and travels axially in slots 204, 206 formed in cylindrical housing 190.

Deployment of the retractor assembly 62 is accomplished by means of a fan adjust collar 208 having a flange 210 in a distal end and a barrel cam slot 212 in a proximal end interconnected by a drive tube 214. Barrel cam slot 212 may either provide a smooth progression (FIG. 20) or may utilize intermediate grooves 216 (FIGS. 22) to give intermediate stops as the blades 68 deploy. A compression spring 218 is disposed between inner bushing 148 and movable block 200 in order to preload the system and to assist in distal movement of enclosure tube 70.

In operation, hooked locking tab 142 of transversely flexible locking member 140 is moved proximally until tab 142 engages and locks in place behind flange 210 in fan adjust collar 208. In this position, enclosure tube 70 is located at its proximalmost position exposing the retractor assembly 62. Fan adjust collar 208 is then rotated relative to cylindrical housing 190 causing transverse camming pin 202 to be driven axially distally by barrel cam slot 212 in slots 204, 206. This relative axial distal motion deploys blades 68 into a fan configuration.

To close the retractor, fan adjust collar 208 is rotated in the opposite direction to move the blades 68 together. Transversely flexible locking member 140 is depressed to disengage hooked locking tab 142 from flange 210. Compression spring 218 assists in the distal movement of enclosure tube 70. Clasp knob is then moved distally until enclosure tube 70 is at its distalmost position enclosing at least a portion of retractor assembly 62.

FIGS. 25-29 illustrate a surgical retractor, indicated generally at 220, utilizing a pistol grip-type handle means 222 and an abbreviated retractor assembly 224. The handle means 222 includes a stationary housing 226 with a depending finger grip 228 integrally formed therewith, and a pivotal arm 230 having a depending finger grip 232 on a proximal end thereof and a rack 234 formed on a distal end. Pivotal arm 230 attached to stationary housing 226 by means of a pivot pin 236. Both the depending finger grip 228 of the stationary housing 226 and the depending finger grip 232 of pivotal arm 230 have provided thereon complementary inward facing racks, 238, 240 respectively, whose teeth 242 progressively interlock to hold pivot arm 230 at a predetermined angular orientation with respect to stationary housing 226.

A longitudinal cavity 244 is provided in an upper portion of stationary housing 226 to accommodate the reciprocal longitudinal motion of bolt assembly 246. This bolt assembly comprises a proximally mounted cylindrical pinion 248 followed distally by a mounting block 250 for fixedly holding center rod 252. A guide tube mounting block 254 is attached distally to mounting block 250 and includes a bolt handle 256 fixed to the guide tube mounting block 254 which handle 256 is guided in axial movement by slot 258 formed in stationary housing 226. Guide tube mounting block 254 is provided with an axial bore 260 therethrough to allow center rod 252 to be driven distally by the interaction of rack 234 and cylindrical pinion 248 as described below.

An endoscopic enclosure tube 262 is fixed to stationary housing 226 and serves to enclose and protect the retractor assembly 224 when it is closed and retracted. Guide tube 264 extends from guide tube mounting block 254, through enclosure tube 262 to attach to a pivot yoke assembly 90 as described above. Center rod 252 extends from mounting block 250, through axial bore 260 and guide tube 264 to attach to slide yoke assembly 88. A rotation knob 265 is rotatably mounted in stationary housing 226 and engages guide tube 264 so as to allow direct rotation of the retractor assembly 224.

The abbreviated retractor assembly 224 operates in a manner similar to that described above with respect to retractor assembly 62, and includes an axial blade 266 (FIG. 29) connected at a proximal end to center rod 252. A pair of angularly deployable blades 268, 270 with serrated longitudinal side edges 272, 274 cooperate with axial blade 266 to assist in the retractor function. Axial blade 266 is texturized along its flat surfaces 276 to assist in gripping and retracting tissue. Blades 268, 270 are provided with a pivot hole 278 in a proximal end and a camming slot 280 located distally to pivot hole 278. A pivot pin 282 mounted in pivot yoke assembly 88 passes through pivot holes 278 and acts as a pivot point for blades 268 and 270. A camming pin 284 is transversely mounted in axial blade 266 (FIG. 29) and rides in camming slots 280 to angularly deploy blades 268 and 270 as the axial blade 266 is reciprocally moved with respect to pivot yoke assembly 88. An axial slot 283 is provided in axial blade 266 proximal to transverse camming pin 284. This slot 283 allows axial blade 266 to move reciprocally with respect to pivot pin 282. A compression spring 286 is disposed between the distal end of axial blade 266 and pivot yoke assembly 88 and is compressed upon deployment of the retractor assembly 224. This compressed force assists in the closure of the blades 268, 270 when the force is released.

To operate surgical retractor 220, bolt handle 256 is moved distally in slot 258 thus moving bolt assembly 246 forward. This action moves the abbreviated retractor assembly 224 out of the distal end of enclosure tube 262 and concurrently engages cylindrical pinion 248 with rack 234. See. FIG. 26. Finger grips 228, 232 are approximated about pivot pin 236 causing rack 234 to drive cylindrical pinion 248 in a proximal direction drawing axial blade 266 proximally relative to pivot yoke assembly 88. Blades 268 and 270 are thus deployed by the motion of cam pin 284 in camming slots 280. Complementary racks 238 and 240 interlock to maintain the blades in a deployed attitude.

To close the retractor 220, teeth 242 of racks 238, 240 are disengaged and, with the assistance of compression spring 286, finger grips 228, 232 are moved apart until rack 234 disengages from cylindrical pinion 248. Bolt assembly 246 can then be drawn proximally to retract the closed blade assembly into enclosure tube 262.

Referring to FIGS. 23, 24 and 30-40 and specifically to FIG. 30, a surgical retractor 288 is shown in accordance with a simplified embodiment of the present invention. The surgical retractor 288 includes a retractor assembly 290 having a housing member 292 with a blade storage cavity 294 formed in a distal end. A transverse bore 296 is formed in a proximal end of housing member 292 and serves to retain pivot pin 298 therein. Referring to FIGS. 23 and 24, a slide yoke assembly 300 interconnects with a distal end of center rod 106 and includes a pair of axial legs 302 with an aligned transverse bore 304 and an aligned, axial slot 306 formed therein. A moving pin 308 is disposed in transverse bore 304 and axial slot 306 serves to enclose pivot pin 298 and permit axial reciprocal motion of the slide yoke assembly 300 relative to pivot pin 298.

A blade assembly 310 is disposed in retractor assembly 290 and includes a pair of inner blades 312 and a pair of outer blades 314. Each of said blades 312, 314 include a pivot bore 316 formed in a proximal end and a cam slot 318 positioned distal to the pivot bore 316. In the embodiment of FIG. 30, the outer edges of blades 312, 314 are provided with serrations 320 to assist in the retractor function. Other modifications including texturized coatings, abrasive surfaces, etc. could also be utilized and are within the scope of the present invention.

Blades 312, 314 are retained in blade storage cavity 294 with pivot pin 298 positioned in pivot bores 316. Moving pin 308 of slide yoke assembly 300 is disposed in cam slots 318 such that reciprocal axial motion of slide yoke assembly 300 relative to housing member 294 causes moving pin 308 to move in cam slots 318 to either deploy or retract blades 312, 314 about pivot pin 298.

An elongated tubular housing assembly 322 is connected to retractor assembly 290 and includes a center rod 106 and a guide tube 108. Center rod 106 extends through guide tube 108 and is connected at a distal end to slide yoke assembly 300 and at a proximal end to handle means 324. Guide tube 108 is attached at a distal end to housing member 292 and at a proximal end to handle means 324. In this embodiment of surgical retractor 288, guide rod 106 is axially fixed in handle means 324. Center rod 106 is adapted for axial reciprocal motion within guide tube 108.

Handle means 324 includes a stationary handle 326 and a pivoting handle 328. Finger loops 330, 332 are provided on the lower ends of handles 326, 328 respectively. Where desired, racks 329, 331 may be provided with the handles 326, 328 as discussed above in order to lock the retractor assembly 290 at a predetermined degree of deployment.

Pivoting handle 328 is pivotally mounted to stationary handle 326 by pivot pin 334. A pivot bushing 336, comprising a pair of disks 338 each having connecting means for interengaging the disks 338 with each other, captures a proximal end of center rod 106 to control axial motion thereof. This pivot bushing 336 retains the proximal end of center rod 106 while permitting the rod 106 to freely rotate therein and maintain the rod 106 in axial alignment with guide tube 108 throughout the entire range of motion of pivoting handle 328.

In preferred embodiments, as shown in FIG. 30, the retractor assembly 290 and the elongated tubular housing assembly 322 are axially rotatable by rotation knob 340 mounted in stationary handle 326. This rotation knob 340 engages bushing 342 attached to guide tube 108. Rotation knob 340 is preferably knurled or provided with ridges to allow for easy manipulation by the user's thumb or fingers. Similarly, bushing 342 may be provided with angular faces of polygonal cross-section cooperating with corresponding faces formed in the stationary handle 326 so as to provide predetermined rotational stops wherein the retractor assembly 290 is maintained at a given angular orientation relative to the handle means 324.

To deploy the retractor assembly 290 of surgical retractor 288, pivoting handle 328 is moved from an initial position (shown in phantom in FIG. 30) to a final position wherein pivot bushing 336 is moved distally into close approximation with stationary handle 326. This motion drives center rod 106 distally through guide tube 108 thereby driving slide yoke assembly 300 with moving pin 308 through cam slots 318 in blades 312, 314. Depending upon the degree of distal movement of center rod 106 relative to guide tube 108, blades 312, 314 are caused to deploy about pivot pin 298 into a fan configuration. See FIG. 30. To close the retractor assembly 290, handles 326 and 328 are approximated causing pivot bushing 336 to move proximally with respect to pivot pin 334. This proximal movement draws center rod 106 and thus moving pin 308 in a proximal direction moving blades 312, 314 into a stacked interleaved configuration in blade storage cavity 294.

Referring now to FIGS. 31-41, there is shown a wide variety of housing member configurations for retractor assemblies. In FIG. 31, housing member 292 includes a streamlined removable tip portion 346 attached at a distal end to protect blade storage cavity 294.

FIGS. 32 and 33 show a housing member 344 integrally formed with guide tube 108 wherein the distal ends are crimped over to form a blunt rectangular end 348 distal to blade storage cavity 294. A transverse bore 304 is formed in housing member 344 to receive stationary pivot pin 298. Aperture 350 serves as an attachment point for bushing 342 to permit rotation of guide tube 108 by rotation knob 340. Similarly, FIGS. 34 and 35 show a housing 344 integrally formed with guide tube 108 with a distal end 352 formed in a blunt cylindrical shape. A transverse bore 304 is formed proximal to blade storage cavity 294 and an aperture 350 interconnects guide tube 108 with bushing 342.

FIGS. 36 and 37 show a closed end housing member 354 having a rounded distal portion 356 with a rectangular cross-section. Proximal to rounded distal portion 356, upper and lower surfaces 358, 360 of housing member 354 are substantially flattened and then ramp out to conform in diameter and cross-section with guide tube 108. A transverse bore 304 is formed in housing member 354 proximal to blade storage cavity 294 to receive pivot pin 298 therein. Blades 362 pivot about pivot pin 298 between a closed position (FIG. 36) and a deployed position (FIG. 36) as described above.

FIGS. 38 and 39 show a streamlined closed end housing member 364 having a configuration somewhat similar in appearance to that of housing 292 of FIG. 31 with the exception that streamlined tip portion 346 is monolithically formed with housing member 364. This embodiment is otherwise similar in operation to that of closed end housing member 354 described above.

Referring to FIGS. 40 and 41, an open end housing member 366 is shown having a blade storage cavity 294 which is open at its distal end 368. Both upper and lower surfaces, 370, 372 are rounded to facilitate smooth insertion into a cannula (not shown). As in the embodiment of FIGS. 36 and 37, upper and lower surfaces 370, 372 of housing member 366 are substantially flattened near the distal end 368 and ramp out to conform in diameter and cross-section with guide tube 108. This embodiment is otherwise similar in operation to that of housing members 354 and 364 above.

The surgical retractor of the present invention is a compact, lightweight and easy to use instrument incorporating many features required during endoscopic surgical procedures which allows the surgeon to use the instrument with one hand thus freeing the other hand for manipulation of other instruments during surgery. The present retractor overcomes many of the disadvantages encountered with prior art devices and provides a precision instrument which is easy to handle and simple to manufacture. While the invention has been particularly shown and described with reference to preferred embodiments thereof, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A surgical retractor comprising:
   handle means including actuation structure;
   housing means attached to said actuation structure of said handle means, said housing means having at least one center element disposed adjacent a guide element for relative reciprocal motion therewith, said center and guide elements having proximal and distal ends; and
   a retractor assembly, including a reciprocal yoke assembly having a slide yoke means, a pivot yoke means, and a plurality of interleaved retractor blades connected together at a pivot pin, said slide yoke means and said pivot yoke means cooperating with said housing means such that relative reciprocal axial movement of said center element and said guide element serves to move said interleaved retractor blades between a closed position and an open position.

2. A surgical retractor as in claim 1 wherein said retractor assembly comprises a fixed pivot yoke means connected at a proximal end to said distal end of said guide element and at a distal end to said pivot pin in said interleaved retractor blades and a slide yoke means connected at a proximal end to said distal end of said center element and at a distal end to camming slots in said interleaved retractor blades, said slide yoke means being axially movable relative to said fixed pivot yoke means.

3. A surgical retractor as in claim 2 wherein said pivot yoke means is monolithically formed proximate a distal end of said guide element of said housing means.

4. A surgical retractor as in claim 1 further comprising an enclosure tube for enclosing at least a portion of said retractor assembly when said blades of said retractor assembly are in said closed position.

5. A surgical retractor as in claim 1 wherein said housing means comprises an elongated tubular structure formed with an elongated center element and a tubular guide element.

6. A surgical retractor as in claim 5 wherein said retractor assembly and at least a distal end of said housing means form an endoscopic portion of said surgical retractor.

7. A surgical retractor as in claim 5 wherein said elongated tubular structure further comprises an enclosure tube surrounding at least a portion of said elongated center element and said tubular guide element.

8. A surgical retractor as in claim 1 wherein said handle means is configured as an axial cylinder having a proximal and distal end.

9. A surgical retractor as in claim 8 wherein said actuation structure comprises a deployment knob connected to a proximal end of said center element and adapted to move said center element axially with respect to said guide element.

10. A surgical retractor as in claim 9 wherein said deployment knob includes camming means engageable with camming surfaces on said handle means to move said center element reciprocally relative to said guide element.

11. A surgical retractor as in claim 8 wherein said actuation structure comprises an inner bushing axially slidably disposed within said axial cylinder to axially move said center element with respect to said guide element.

12. A surgical retractor as in claim 8 further comprising an enclosure tube telescopically surrounding said center element and said guide element, said enclosure tube being slidably mounted in said handle means for reciprocal sliding motion therein.

13. A surgical retractor as in claim 1 wherein said handle means is configured as a pistol grip having at least one pivoting handle.

14. A surgical retractor as in claim 13 wherein said actuation structure comprises a pinion attached to said center element and engaged by a corresponding rack actuated by relative reciprocal motion of said at least one pivoting handle.

15. A surgical retractor as in claim 13 wherein said actuation structure comprises a pivot bushing retained in at least one of said pivoting handles and connected to said center element, said guide element being connected to said housing such that reciprocal motion of said at least one pivoting handle reciprocates said center element relative to said guide element.

16. A surgical retractor as in claim 13 further comprising an enclosure tube telescopically surrounding said center element and said guide element, said enclosure tube being slidably mounted in said handle means for reciprocal sliding motion therein.

17. A surgical retractor as in claim 1 wherein at least one of said interleaved retractor blades is provided with retraction enhancing means.

18. A surgical retractor as in claim 17 wherein said retraction enhancing means comprises a plurality of serrations.

19. A surgical retractor as in claim 17 wherein said retraction enhancing means comprises a texturized surface.

20. A surgical retractor as in claim 1 wherein said retractor assembly further comprises a blade storage cavity connected to said guide element.

21. A surgical retractor as in claim 20 wherein said retractor assembly includes a streamlined tip portion formed on distal end thereof.

22. A surgical retractor as in claim 20 wherein said blade storage cavity is open at a distal end thereof and defined only by a tip portion, a bottom portion and a rear portion.

23. A surgical retractor as in claim 1 wherein said interleaved retractor blades are deployed in a symmetrical fan configuration.

24. A surgical retractor as in claim 1 wherein said interleaved retractor blades are deployed in an asymmetrical fan configuration.

25. A surgical retractor as in claim 1 further comprising rotation means which permits rotation of said retractor assembly relative to said handle means.

26. A surgical retractor as in claim 1 further comprising sequential stop means for engaging said actuation structure to hold said interleaved retractor blades in intermediate positions of deployment between said open position and said closed position.

27. A surgical retractor as in claim 26 wherein said sequential stop means is adapted to engage said actuation structure to hold said interleaved retractor blades in intermediate positions of deployment between said open and said closed position.

28. A surgical retractor comprising:
handle means including actuation structure;
endoscopic tubular housing means attached to said actuation structure of said handle means, said endoscopic tubular housing means including an elongated center element axially slidably disposed within an elongated tubular guide element for reciprocal motion therein, and center and guide elements having proximal and distal ends; and
an endoscopic retractor assembly including a reciprocal yoke assembly having a slide yoke and a pivot yoke, said slide yoke and said pivot yoke both cooperating at distal ends thereof with a plurality of interleaved retractor blades, said slide yoke being connected on a proximal end to said elongated center element and said pivot yoke being connected on a proximal end to said elongated tubular guide element such that reciprocal motion of said center element within said guide element serves to move said interleaved retractor blades between a closed position and an open position.

29. A surgical retractor as in claim 28 further comprising an enclosure tube for enclosing at least a portion of said retractor assembly when said blades of said retractor assembly are in said closed position.

30. A surgical retractor as in claim 28 wherein said handle means is configured as an axial cylinder having a proximal and distal end.

31. A surgical retractor as in claim 30 further comprising an enclosure tube telescopically surrounding said center element and said guide element, said enclosure tube being slidably mounted in said handle means for reciprocal sliding motion therein.

32. A surgical retractor as in claim 28 wherein said handle means is configured as a pistol grip having at least one pivoting handle.

33. A surgical retractor as in claim 32 further comprises an enclosure tube telescopically surrounding said center element and said guide element, said enclosure tube being slidably mounted in said handle means for reciprocal sliding motion therein.

34. A surgical retractor as in claim 28 wherein said retractor assembly further comprises a blade storage cavity connected to said guide element.

35. A surgical retractor as in claim 28 wherein said interleaved retractor blades are deployed in a symmetrical fan configuration.

36. A surgical retractor as in claim 28 wherein said interleaved retractor blades are deployed in an asymmetrical fan configuration.

37. A surgical retractor as in claim 28 further comprising rotation means which permits rotation of said retractor assembly relative to said handle means.

38. A surgical retractor as in claim 28 wherein said pivot yoke is monolithically formed proximate a distal end of said guide element of said housing means.

39. A surgical retractor comprising:
cylindrical handle means including actuation structure;
endoscopic tubular housing means including an elongated center element axially slidably disposed within an elongated tubular guide element for reciprocal motion therein, said center and guide elements being disposed within an enclosure tube; and
an endoscopic retractor assembly including a reciprocal yoke assembly having a slide yoke and a pivot yoke, said slide yoke and said pivot yoke both being connected at distal ends thereof to a plurality of interleaved flat retractor blades, said blades each having a pivot bore in a proximal end and a cam slot distal to said pivot bore, said slide yoke having a transverse moving pin disposed in each of said cam slots of said blades and said pivot yoke having a transverse pivot pin disposed in each of said pivot bores of said blades, said slide yoke being connected on a proximal end to said elongated center element and said pivot yoke being connected on a proximal end to said elongated tubular guide element such that when said endoscopic retractor assembly is clear of said enclosure tube, reciprocal motion of said center element within said guide element serves to move said interleaved retractor blades between a closed position and an open position.

40. A surgical retractor as in claim 39 wherein said actuation structure includes an inner bushing disposed within an outer bushing, said outer bushing being attached to said enclosure tube and movable between a first distal position wherein said retractor assembly is enclosed and a second proximal position wherein said retractor assembly is uncovered, said inner bushing being connected to said elongated tubular guide member and including an axial bore for accommodating said elongated center element, said actuation structure further including a deployment knob and camming structure, said deployment knob being connected to a proximal portion of said elongated center element and engageable with said camming structure to reciprocally move said center element with respect to said guide element.

41. A surgical retractor as in claim 40 wherein said actuation structure further comprises spring means disposed adjacent said camming structure for assisting in movement of said center rod relative to said guide rod.

42. A surgical retractor as in claim 40 further comprising stops formed in said camming structure for engaging said deployment knob to hold said interleaved retractor blades in intermediate positions of deployment between said open position and said closed position.

43. A surgical retractor comprising:
pistol grip handle means having a stationary handle and a pivoting handle including actuation structure;
endoscopic tubular housing means including an elongated center element axially slidably disposed within an elongated tubular guide element for reciprocal motion therein, said center and guide elements being disposed within an enclosure tube; and
an endoscopic retractor assembly including a reciprocal yoke assembly having an axial blade and a pivot yoke, said axial blade and said pivot yoke both cooperating at distal ends thereof with a plurality of interleaved flat retractor blades each having a pivot bore in a proximal end and a cam slot distal to said pivot bore, said axial blade having a transverse moving pin attached thereto and engaging said cam slots of said retraction blades and said pivot yoke having a transverse pivot pin disposed in each of said pivot bores of said retractor blades, said axial blade being connected on a proximal end to said elongated center element and said pivot yoke being connected on a proximal end to said elongated tubular guide element such that when said endoscopic retractor assembly is clear of said enclosure tube, reciprocal motion of said center element within said guide element serves to move said interleaved retractor blades between a closed position and an open position.

44. A surgical retractor as in claim 43 wherein said enclosure tube is fixed to said housing means and said actuation structure includes a guide tube mounting block and a center element mounting block disposed in a longitudinal cavity formed in said pistol grip housing means, said center rod mounting block further including a pinion formed on a proximal end thereof such that when guide tube mounting block and center element mounting block are moved to a distal position moving retractor assembly beyond said enclosure tube, said pinion is engageable with a rack formed on said pivoting handle to deploy said retractor assembly.

45. A surgical retractor as in claim 43 wherein said housing means further comprises rotation means for axially rotating said retractor assembly relative to said handle means.

46. A surgical retractor as in claim 43 wherein said interleaved retractor blades are deployed in an asymmetrical fan configuration.

47. A surgical retractor comprising:
pistol grip handle means having a stationary handle and a pivoting handle, said handle mens including actuation structure;
endoscopic tubular housing means including an elongated center element coaxially slidably disposed within an elongated tubular guide element for reciprocal motion therein in response to movement of said pivoting handle; and
an endoscopic retractor assembly including a reciprocal yoke assembly having a slide yoke means and a pivot yoke means, said pivot yoke means being monolithically formed in a distal end of said guide tube, said pivot yoke means and said slide yoke means being connected at distal ends thereof to a plurality of interleaved flat retractor blades, said blades each having a pivot bore in a proximal end and a cam slot distal to said pivot bore, said slide yoke means having a transverse moving pin disposed in each of said cam slots of said blades and said pivot yoke means having a transverse pivot pin disposed in each of said pivot bores of said blades, said slide yoke means being connected on a proximal end to said elongated center element and adapted for reciprocal motion with respect to said pivot yoke means such that movement of said pivoting handle serves to move said interleaved retractor blades between a closed position and an open position.

48. A surgical retractor as in claim 47 wherein said actuation structure includes a pivot bushing rotatably positioned in said pivoting handle for maintaining and coaxially moving said elongated center element with respect to said elongated guide element.

49. A surgical retractor as in claim 47 wherein said retractor assembly further comprises a blade storage cavity formed in a distal end of said elongate tubular guide element.

50. A surgical retractor as in claim 47 wherein at least one of said interleaved retractor blades is provided with retraction enhancing means.

51. A surgical retractor as in claim 47 wherein said interleaved retractor blades are deployed in a symmetrical fan configuration.

52. A surgical retractor as in claim 47 wherein said housing means further comprises rotation means for axially rotating said retractor assembly relative to said handle means.

53. A surgical retractor as in claim 47 further comprising sequential stop means for engaging said actuation structure to hold said interleaved retractor blades in intermediate positions of deployment between said open position and said closed position.

54. A surgical retractor as in claim 47 wherein said retractor blades are deployed to an angle less than 180° relative to said center element.

55. A surgical retractor as in claim 54 wherein said retractor blades are deployed at an acute angle relative to said center element.

56. A surgical retractor as in claim 47 wherein said retractor assembly comprises at least three retractor blades.

57. A surgical retractor comprising:
handle means including actuation structure;
housing means attached to said actuation structure of said handle means, said housing means having at least one center element disposed adjacent a guide element for relative reciprocal motion therewith, said center and guide elements having proximal and distal ends; and
a retractor assembly, including a reciprocal yoke assembly having a slide yoke means, a pivot yoke means, and a plurality of interleaved retractor blades connected together at a pivot pin, said slide yoke means and said pivot yoke means cooperating with said housing means such that relative reciprocal axial movement of said center element and said guide element serves to move said interleaved retractor blades between a closed position and an open position while maintaining a fixed longitudinal length of the retractor assembly.

58. A surgical retractor comprising:
handle means including actuation structure;
endoscopic tubular housing means attached to said actuation structure of said handle means, said endoscopic tubular housing means including an elongated center element axially slidably disposed within an elongated tubular guide element for reciprocal motion therein, and center and guide elements having proximal and distal ends; and
an endoscopic retractor assembly including a reciprocal yoke assembly having a slide yoke and a pivot yoke, said slide yoke and said pivot yoke both cooperating at distal ends thereof with a plurality of interleaved retractor blades, said slide yoke being connected on a proximal end to said elongated center element and said pivot yoke being connected on a proximal end to said elongated tubular guide element such that reciprocal motion of said center element within said guide element serves to move said interleaved retractor blades between a closed position, at least one intermediate position and an open position.

* * * * *